United States Patent [19]

Bühler

[11] Patent Number: 5,443,792
[45] Date of Patent: Aug. 22, 1995

[54] PIPETTING DEVICE

[75] Inventor: Jürg Bühler, Rothenburg, Switzerland

[73] Assignee: Hoffmann-La Roche Inc., Nutley, N.J.

[21] Appl. No.: 325,732

[22] Filed: Oct. 19, 1994

Related U.S. Application Data

[63] Continuation of Ser. No. 16,405, Feb. 11, 1993, abandoned.

[30] Foreign Application Priority Data

Feb. 13, 1992 [CH] Switzerland .................. 428/92

[51] Int. Cl.$^6$ .......................................... G01N 35/10
[52] U.S. Cl. ...................................... 422/67; 422/100; 422/106; 73/863.01
[58] Field of Search ........... 73/863.01, 864.25, 864.24; 422/63, 64, 65, 67, 81, 100, 106, 108; 436/54

[56] References Cited

U.S. PATENT DOCUMENTS

| | | | |
|---|---|---|---|
| 4,757,437 | 7/1988 | Nishimura | 73/863.01 X |
| 5,138,868 | 8/1992 | Long | 73/1 R |
| 5,270,210 | 12/1993 | Weyrauch et al. | 436/43 |

FOREIGN PATENT DOCUMENTS

| | | |
|---|---|---|
| 252471 | 7/1987 | European Pat. Off. |
| 4113377 | 4/1991 | Germany |
| 87/06008 | 10/1987 | WIPO |
| 91/16675 | 10/1991 | WIPO |
| 92/15017 | 9/1992 | WIPO |

OTHER PUBLICATIONS

Patent Ab., vol. 14, No. 498 (P-1124) (Oct. 30, 1990) for JP-A-2203.
Derwent Abstract No. 91-326807 for DE 4 113 377.
Patent Ab., vol. 15, No. 36 (E-1027) (Jan. 29, 1991) for JP-A-2 275 700.
Patent Ab., vol. 15, No. 33 (P-1158) (Jan. 1991) for JP-A-2 272 604.
Patent Ab., vol. 8, No. 164 (M-313) (Jul. 28, 1984) for JP-A-59 059 337.

*Primary Examiner*—Jeffrey R. Snay
*Attorney, Agent, or Firm*—George M. Gould; George W. Johnston; John P. Parise

[57] ABSTRACT

A pipetting device contains a pipetting needle connected to metering device for transferring a volume of liquid from a primary vessel to a secondary vessel. Primary vessel and secondary vessels are disposed on the same or different vessel carrier units, and each vessel has a clearly defined position relative to the vessel carrier unit. Additionally, a device is provided for controlling conveyance of the pipetting needle in three directions. The controlling device controls the metering device and the conveyance device. The pipetting device independently determines coordinates of the pipetting positions for each vessel carrier unit. For each vessel carrier unit at least one reference member, which is part of the vessel carrying unit or is directly and permanently connected thereto, may be provided. These vessel carrier units have flat surfaces which are accessible to sensing the pipetting needle. The control device is capable of moving the pipetting needle to each of the surfaces of the reference member, to determine a reference point. Contact can also be determined between the pipetting needle and each of the surfaces of the reference member. Each of these surfaces determines a reference point.

10 Claims, 8 Drawing Sheets

PIPETTING DEVICE

This is a continuation of application Ser. No. 08/016,405, filed Feb. 11, 1993, now abandoned.

FIELD OF THE INVENTION

The invention relates to a pipetting device which is a component of an automatic analyzer, for example, an automatic analyzer which analyzes biological samples.

BACKGROUND OF THE INVENTION

A conventional pipetting process in an automatic analyzer typically involves, for example, removal of a given volume of reagent from a primary vessel, for example, a reagent container, and delivery thereof to a secondary vessel, for example, a reaction vessel. A conveying device conveys the pipetting needle from one target position to the next. In each target position the automatically controlled metering device removes or delivers the desired volume of liquid.

In the three-dimensional rectangular coordinate system of the conveying device, the primary and secondary vessels are disposed in containers on carrier plates extending parallel to the XY plane of the coordinate system. When the conveying device moves the pipetting needles to a target position, it first moves the needle in a plane parallel to the XY plane until it is above the target vessel, after which it moves the needle downwards into the correct position for removing liquid from a primary vessel or delivering liquid to a secondary vessel.

If the conveying device is to convey the pipetting needle to exactly the right target position in the XY plane, i.e. exactly above a primary or secondary vessel, the following conditions must be fulfilled: the device controlling the conveying device must receive an input signal containing the X and Y coordinates of the target position in order to actuate the conveying device accordingly; the primary and secondary vessel must be at exactly the right position; the pipetting needle must be straight, i.e. must not have any deformation; and the conveying device must be adjusted in each conveying direction, i.e. in each conveying direction a position must be defined and serve as a reference position.

In order to adjust the conveying device of the pipetting needle, in previously-known pipetting devices of the aforementioned kind, the reference position of one component of the device for conveying the pipetting needle is manually adjusted for each direction of conveyance. The known adjustment process is based on adjusting the position of mechanical parts of the conveying device in relation to reference points having positions (called zero positions) defined e.g. by light barriers. One such zero position must be defined for each conveying direction. The zero positions must also be adjusted until the distance of the light barrier from the primary vessels has a defined value. When the device is used, the aforementioned mechanical devices are automatically moved to their zero positions whenever the device is switched on.

This known method of adjustment has the following disadvantages:

(1) Relatively considerable labor and time is required for basic adjustment of the device conveying the pipetting needle when the device is set up.

(2) The adjustment process cannot take account of possible deformations of the pipetting needle during its working life, i.e. even if the reference position of the aforementioned components of the conveying device is relatively accurately adjusted, it may happen that a slightly bent pipetting needle misses its target.

(3) The accuracy of adjustment of the zero positions decreases with ageing of the light sources of the light barriers. The brightness and width of the light beam vary with the age of the light source. This results in a corresponding change in the zero positions. To take account of this and to ensure reliable operation of the pipetting devices, the zero positions have to be readjusted by a service engineer after some years. This readjustment also requires a relatively large expense of labor and time.

(4) The accuracy attainable by the known adjustment of the reference position is limited by the fact that a number of mechanical components are inserted between the pipetting needle and the element whose reference position is adjusted. The accuracy with which the needle can be positioned by the conveying device is therefore limited by the sum of the conventional deviations in the dimensions of the aforementioned components and by the spaces between the components.

The known adjustment method is therefore unsuitable for pipetting devices where the needle-conveying device has to be very accurately adjusted and manual adjustment work is undesirable. This is the case e.g. in pipetting devices in modern automatic analyzers. In these, a relatively large number of primary vessels have to be disposed in a relatively small space, and consequently the pipetting needle has to be exactly positioned relative to the individual primary or secondary vessels to ensure reliable pipetting. Exact positioning should also be obtained with minimum labor.

International Patent Application Publication No. WO 91/16675 describes an automatic pipetting device, in which the vessel carrier units each carry an arrangement of vessels, each vessel carder unit being disposed on a predetermined defined position on a working surface, and wherein a single reference member is provided on a given point of the working surface and is permanently and directly connected to the working surface and serves for adjustment of the needle-conveying system. In this known pipetting device, the pipetting needle is connected to a sensor circuit. For adjustment of the needle-conveying system, the needle is used to detect the position of the walls of the single reference member. An important disadvantage of this known device is that the adjustment accuracy that can be achieved therewith is limited by mechanical tolerances between the single reference member and the individual pipetting positions, as well as by the fact that any somewhat inaccurate positioning of the vessel carrier units or deformation of the pipetting needle are disregarded for the adjustment. The consequences of inaccurate adjustment are catastrophic in a system which relies on very accurate adjustment. A pipetting needle incorrectly guided for this reason not only misses its targets, but also damages other system components such as reaction vessels and reagent containers. In addition, the pipetting needle itself may be damaged (deformed) and even broken.

SUMMARY OF THE INVENTION

The invention relates to a pipetting device containing a pipetting needle connected to a metering device for transferring a volume of liquid from a primary vessel to a secondary vessel. The primary vessel and the secondary vessel are disposed on the same or on different vessel carrier units and each vessel has a given clearly defined position relative to the vessel carrier unit carrying it. Further included is a device for controlled conveyance of the pipetting needle in three dimensional directions perpendicular to one another, and a device for controlling the metering device and the conveying device.

The invention also relates to a method of automatically conveying a needle of an automatic pipetting device to a number of pipetting positions by means of a conveying device, each pipetting position corresponding to the position of a given vessel in an arrangement of vessels disposed in the pipetting device, the conveying device being designed to move the pipetting needle in three directions perpendicular to one another and each direction being parallel to one of the coordinate axes of the conveying device.

The aim of the invention is to provide a pipetting device which can obviate the aforementioned disadvantages, i.e. a pipetting device so constructed as to ensure accurate conveyance of the needle to target positions. Another aim of the invention is to provide a method of automatically conveying the needle of an automatic pipetting device, so as to ensure accurate conveyance of the needle to target positions.

The first part of the aforementioned problem is solved according to the invention by a pipetting device characterized in that the following components are provided in the pipetting device in addition to those described above:

a) for each vessel carrier unit, there is provided at least one reference member, which is part of the vessel carrier unit or is directly and permanently connected thereto, and which has flat surfaces which are accessible to sensing with the pipetting needle, b) control means is contained in the control device for causing the pipetting needle to be conveyed to each of the surfaces of the at least one reference member, such surfaces each determining a reference point, and c) there also is provided means for detecting contact between the pipetting needle and each of the surfaces of the at least one reference member, the surfaces each determining a reference point.

The second part of the problem is solved according to the invention by a method characterized in that at least one reference member is used to determine the coordinates of the pipetting positions for a given position of each vessel carrier unit in the pipetting device, and flat surfaces of the at least one reference member are sensed with the pipetting needle in order to measure coordinates of reference points.

The main advantages of the pipetting device and method according to the invention are as follows:

a) The reference position of the needle-conveying device is very accurately adjusted in each conveying direction, X, Y, Z, because the position of the reference points for the conveying device is determined by the needle itself, and because each reference member is a part of a vessel carrier unit or is permanently and directly connected thereto, so that the positions of the reference points are clearly defined and invariable relative to the target positions of the pipetting needle.

b) Possible slight deformations in the pipetting needle have no influence on the accuracy of adjustment of its reference position. After the needle-conveying device has been adjusted according to the invention, even a slightly bent needle reaches its target with great accuracy.

c) Even if the carrier plate is somewhat inaccurately positioned in the analyzer or if the rails bearing the conveying system are not exactly parallel, this has no influence on the accuracy of adjustment of the needle-conveying device.

d) The adjustment of the needle-conveying device according to the invention is completely automatic and therefore requires no manual labor.

A preferred embodiment of the invention is characterized in that the at least one reference member has three flat surfaces perpendicular to one another, the position of each such surface defining the coordinate of a reference point in one of the three-dimensional conveying directions (X, Y, Z).

BRIEF DESCRIPTION OF THE DRAWINGS

An embodiment of the invention will now be described with reference to the accompanying drawings in which.

DETAILED DESCRIPTION OF THE INVENTION

Figure 1:
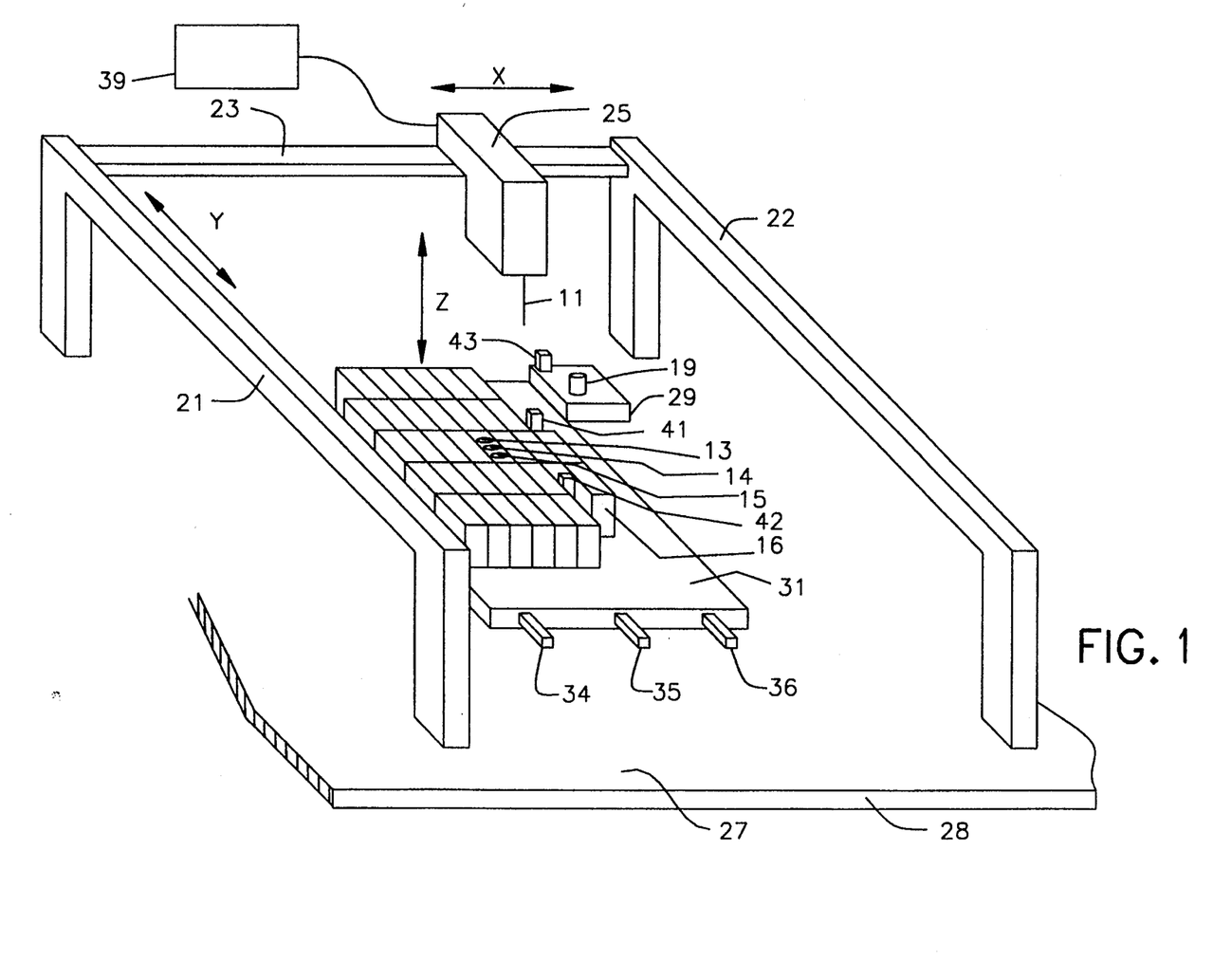
FIG. 1 is a perspective view of a pipetting device according to the invention.

As FIG. 1 diagrammatically shows, a pipetting device according to the invention contains a pipetting needle 11 connected to a metering device (not shown in FIG. 1) for transferring volumes of liquid from primary vessels 13, 14, 15, e.g. reagent containers, to one or more secondary vessels 19, e.g. reaction vessels in which e.g. a biological sample is mixed with a reagent.

The metering device is e.g. an automatically controlled metering syringe which is contained in a carriage 25 and connected by a tube to the pipetting needle.

The pipetting device according to FIG. 1 also comprises an arrangement for controlled conveying of the pipetting needle in three dimensional directions X, Y, Z perpendicular to one another. This arrangement comprises a carriage 25 which carries the pipetting needle 11 and contains a drive for moving the needle in the Z direction. The carriage 25 is moveable in the X direction along the rail 23 by a suitable drive. This rail 23 is moveable along the rails 21 and 22 in the Y direction by means of a suitable drive.

The rails 21, 22 are fixed on a baseplate 27. Provided on this baseplate is a surface on which the carrier plate 31 together with primary vessels is to be placed. To facilitate suitable positioning of the carrier plate 31 on the baseplate 27, surface 28 is provided, for example, with guide ribs 34, 35 36 fitting corresponding grooves in the carrier plate 31.

To control the metering device and the arrangement for conveying the pipetting needle, the pipetting device according to FIG. 1 contains a control device 39.

With the device shown in FIG. 1, for example, a volume of reagent can be pipetted from a reagent container 13 (primary vessel) disposed on a removable carrier plate 31 (first vessel carrier unit) to a reaction vessel 19 (secondary vessel) disposed in a processing device 29 (second vessel carrier unit).

As in the above exemplified embodiment, the primary vessels and secondary vessels can be disposed on different vessel carrier units. Both vessels may alternatively be disposed in the same vessel carrier unit. In a processing device (vessel carrier unit) functionally connected to the pipetting device, it is possible, for example, to pipette a mixture of sample and reagent from one reaction vessel (primary vessel) to another reaction vessel (secondary vessel).

Within the scope of the invention the vessel carrier units may also have different forms and functions. For example, a sample rack carrying a number of sample cups may be a vessel carrier unit. Each vessel carrier unit may also carry one or more vessels.

In the exemplified embodiment shown in FIG. 1, the carrier plate 31 and the processing device 29 are disposed on the same baseplate 27 but this is not essential within the scope of the invention.

Figure 2:
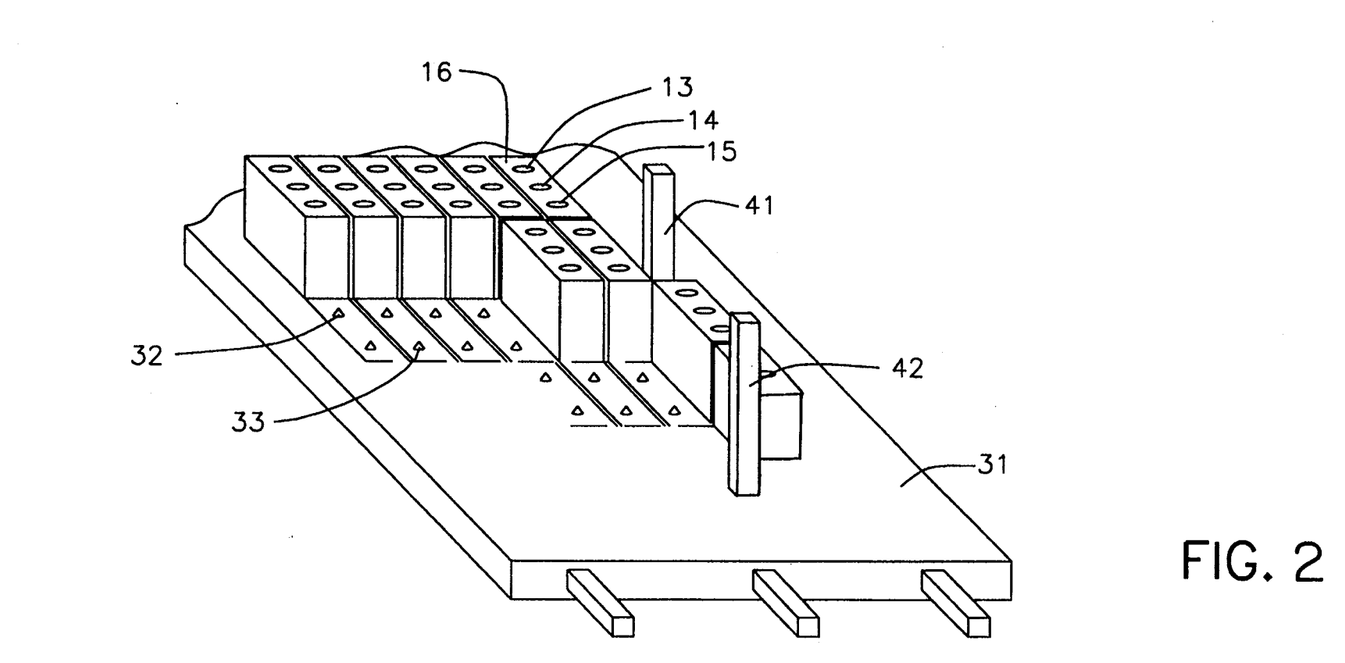
FIG. 2 is a perspective view of the carrier plate 31 in FIG. 1 and some vessel containers 16 disposed on it.

FIG. 2 shows a matrix arrangement of containers 16 on the carrier plate 31. As shown in FIG. 5, each of the vessel containers 16 contains three primary vessels 13, 14, 15. The carrier plate 31 has an arrangement of projections 32, 33 which co-operate with openings 75, 76 in the base 69 of each vessel container 16 as described hereinafter with reference to FIGS. 4 and 5, in order accurately to position the containers 16 on the plate 31 and thus accurately position the primary vessels 13, 14, 15 thereon, so that each primary vessel occupies a unique given position on the carrier plate 31.

Figure 3:
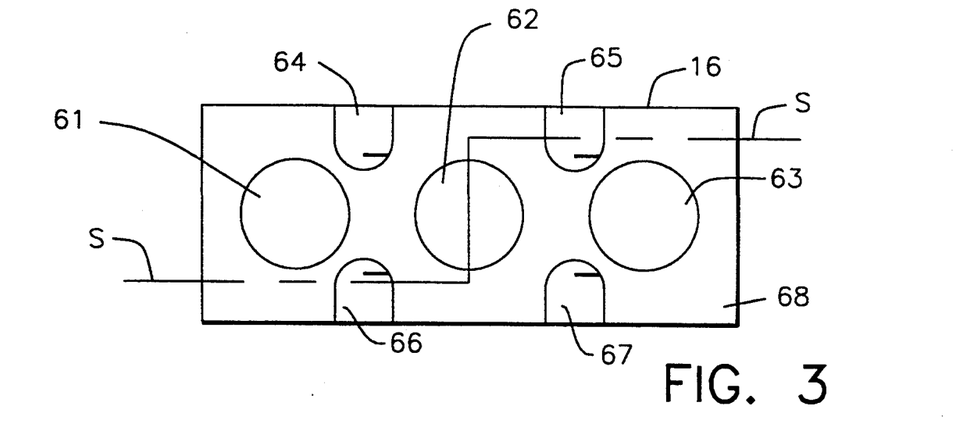
FIG. 3 is a plan view of one of the containers 16 in FIGS. 1 and 2.
Figure 4:
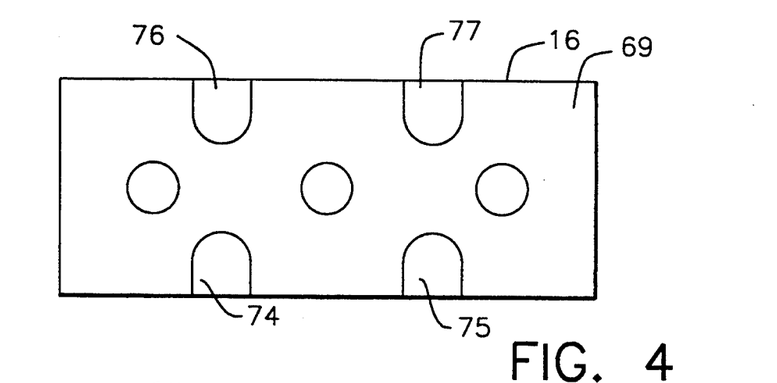
FIG. 4 is a view from underneath one of the containers 16 in FIGS. 1 and 2.
Figure 5:
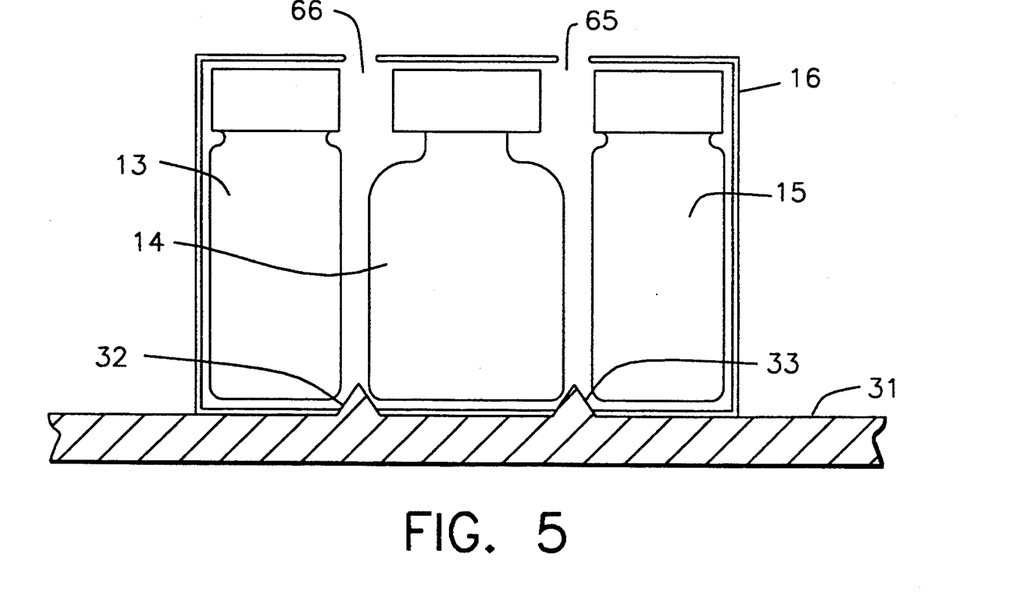
FIG. 5 is a sectional view of a container 16 and the corresponding segment of the carrier plate 31 underneath it, along line S—S in FIG. 3.

FIGS. 3-5 show some views of one of the vessels 16 in FIG. 1. The container has a removable cover 68. As the plan view in FIG. 3 shows, the cover 68 of container 16 has three circular openings 61, 62, 63 providing respective access to one of the primary vessels in the container. During pipetting, the needle is inserted through the openings and through the pierceable cover of the primary vessels 13, 14, 15. The cover 68 of vessel 16 also has openings 64, 65, 66, 67. The base 69 of container 16 has openings 74, 75, 76, 77 for positioning the container 16.

FIG. 5 shows a cross-section of the vessel container along line SS in FIG. 3. The cross-section shows the arrangement of primary vessels 13, 14, 15 in the container 16 and the cooperation of the openings 76, 75 with projections 32, .33 on the carrier plate 31.

In order to automatically adjust the reference positions of the needle-conveying device in the pipetting device of the invention according to FIG. 1, the following components are provided in the pipetting device:

a) for each vessel carrier unit 31 or 29 at least one reference member 41, 42, and 43, which either is part of the vessel carrier unit 31 or 29 or is directly and permanently connected thereto, which reference member has fiat surfaces which are accessible to sensing with the pipetting needle. According to FIG. 1, the processing device 29 has a single reference member 43 and the carrier plate 31 has two reference members 41 and 42;

b) control means contained in the control device 39 for causing the pipetting needle to be conveyed to each of the surfaces 51, 52, 53 of the at least one reference member 41, 42, 43, such surfaces each determining a reference point, and c) means (not shown in FIG. 1) for detecting contact between the pipetting needle 11 and each of the surfaces 51, 52, 53 of the at least one reference member 41, 42, 43, said surfaces each determining a reference point. The means for detecting such contacts are preferably contained in the control device 39.

Figure 6:
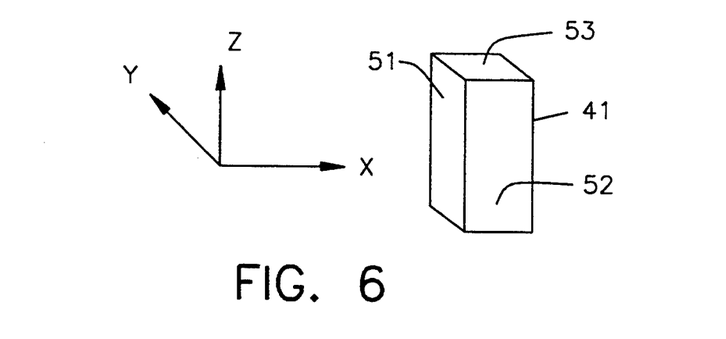
FIG. 6 is a perspective view of the reference member 41 in FIG. 1.

As shown in FIGS. 1, 2 and 6 in the case of the reference member 41, each reference member used according to the invention has three outer surfaces at right angles to one another, the position of each such surface defining the coordinates of a reference point in one of the conveying directions X, Y, Z. The reference members preferably have the form shown in FIGS. 1, 2 and 6. Alternatively, suitable surfaces of a processing device or other parts of the pipetting device may be used as reference members.

Figure 11:
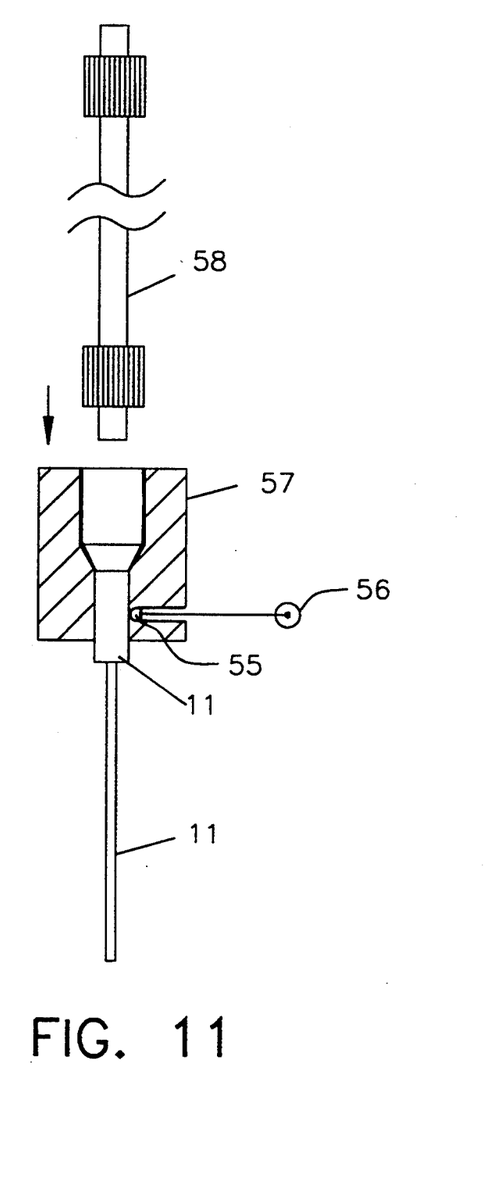
FIG. 11 is a longitudinal section through the pipetting needle 11 in FIG. 1 and the associated connections.

FIG. 11 is a longitudinal section through the needle 11 in FIG. 1 and the associated connections. The needle 11, which is electrically conductive, is held by an electrically non-conducting connecting member 57 made e.g. of plastics. A tube 58 connectable thereto connects the needle to the aforementioned metering device. An electrically conductive connecting element 55 disposed in a side bore in the connecting member 57 connects the needle 11 to a level sensor via a coaxial cable. The device measures a change in impedance between the needle and the electric earth of the entire device in order to generate an electric signal which marks the time at which the needle 11 during its downward motion reaches the free surface of the liquid in a container.

According to the invention, the aforementioned level sensor is also used to detect contact between the pipetting needle and each surface 51, 52, 53 of the reference members 41, 42, 43 determining a respective reference position, when the needle-conveying system is adjusted by moving the needle 11 to each of the aforementioned surfaces, as diagrammatically shown in FIGS. 7 to 10.

Figure 7:
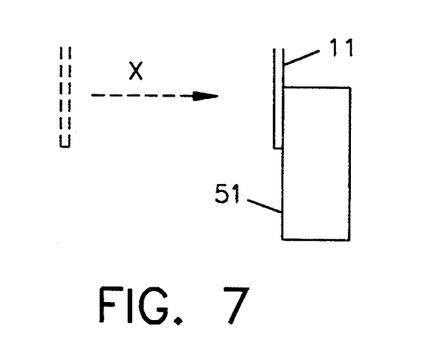
FIGS. 7–10 are diagrams each showing the motion of the pipetting needle relative to each of the surfaces 51, 52, 53 of the reference member 41 in FIG. 6.
Figure 8:
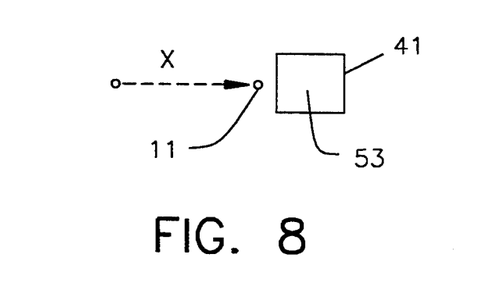
Figure 9:
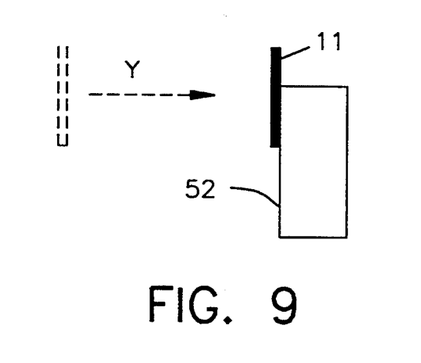
Figure 10:
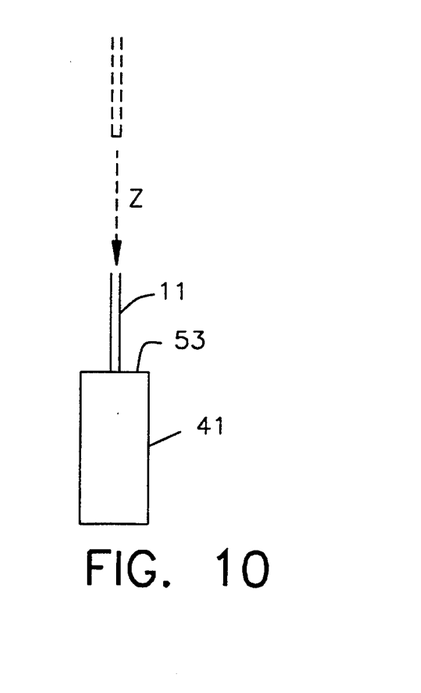

FIG. 8 is a plan view of the motion, diagrammatically shown in FIG. 7, of the needle 11 towards the surface 51 of the reference member 41.

In order to determine a reference position in the X direction, the conveying system first moves the needle relatively quickly to a first position, shown in chain lines in FIG. 7, and thence in very short steps and relatively slowly to the surface 51, until contact between the surface and the needle is detected by the level sensor. As shown in FIG. 8, the needle is moved along a straight line which ideally extends through the middle of the reference member 41. The needle is sure to reach the reference member in every case, since the coordinates of the normal position of the reference member are known to the control device and the reference member has a given width.

Detection of reference positions in the Y and Z directions is carried out in the same way as detection of a reference position in the X direction.

Figure 12:
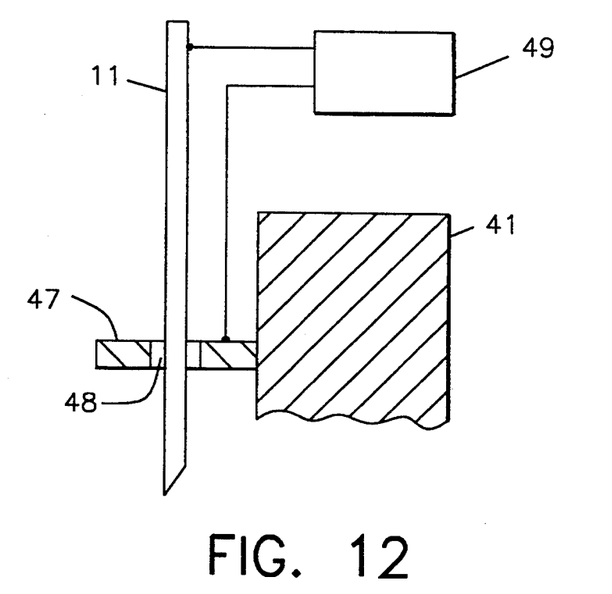
FIG. 12 is a diagrammatic cross-section of a preferred embodiment of the reference member 41 in FIG. 6.

As shown in FIG. 12, in a preferred embodiment of the pipetting device according to the invention, one of the reference members 41-43, e.g. reference member 41, is connected to a test member 47, which has a straight bore 48, the diameter of which is just somewhat larger than the diameter of the pipetting needle, so that a straight pipetting needle can be introduced through the bore without contact occurring between the pipetting needle and the test member. An electric circuit 49 is provided to signal such contact. This circuit preferably comprises the above-mentioned level sensor, which is also used in sensing the surfaces with the pipetting needle.

Figure 13:
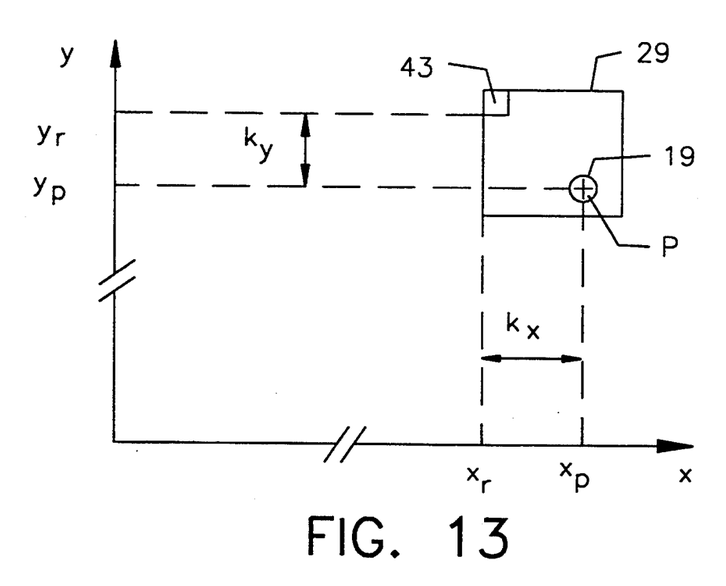
FIG. 13 is a plan view of the processing device 29 in FIG. 1.

FIG. 13 is a plan view of the processing device 29 shown in FIG. 1. This vessel carrier unit contains a pipetting position P in which a reaction vessel 19 is disposed and carries a reference member 43 permanently connected to the processing device 29. The reference member 43 enables reference positions to be defined in the X, Y and Z direction and thus ensure accurate positioning of the pipetting needle 11 in the pipetting position P by means of the needle-conveying device. In the case of the processing device 29, a single reference member is adequate for the purpose because the structural properties of the system are such as to enable it to be assumed that the surfaces 51-53 of the reference member are disposed parallel to the axes of the coordinate systems so that no angle of deviation has to be taken into account.

The coordinates $x_p$, $y_p$, $z_p$ of the pipetting position P in FIG. 13 are defined as follows $$x_p = x_r + k_x; \; y_p = Y_r - k_y; \; \text{and} \; z_p = z_r - k_z$$

where $x_r$, $Y_r$, $z_r$ are the measured coordinates of the reference surfaces of the reference member 43 and $k_x$, $k_y$ are distances shown in FIG. 13. $k_z$ is a corresponding distance (not shown in FIG. 13) in the Z direction.

Figure 14:
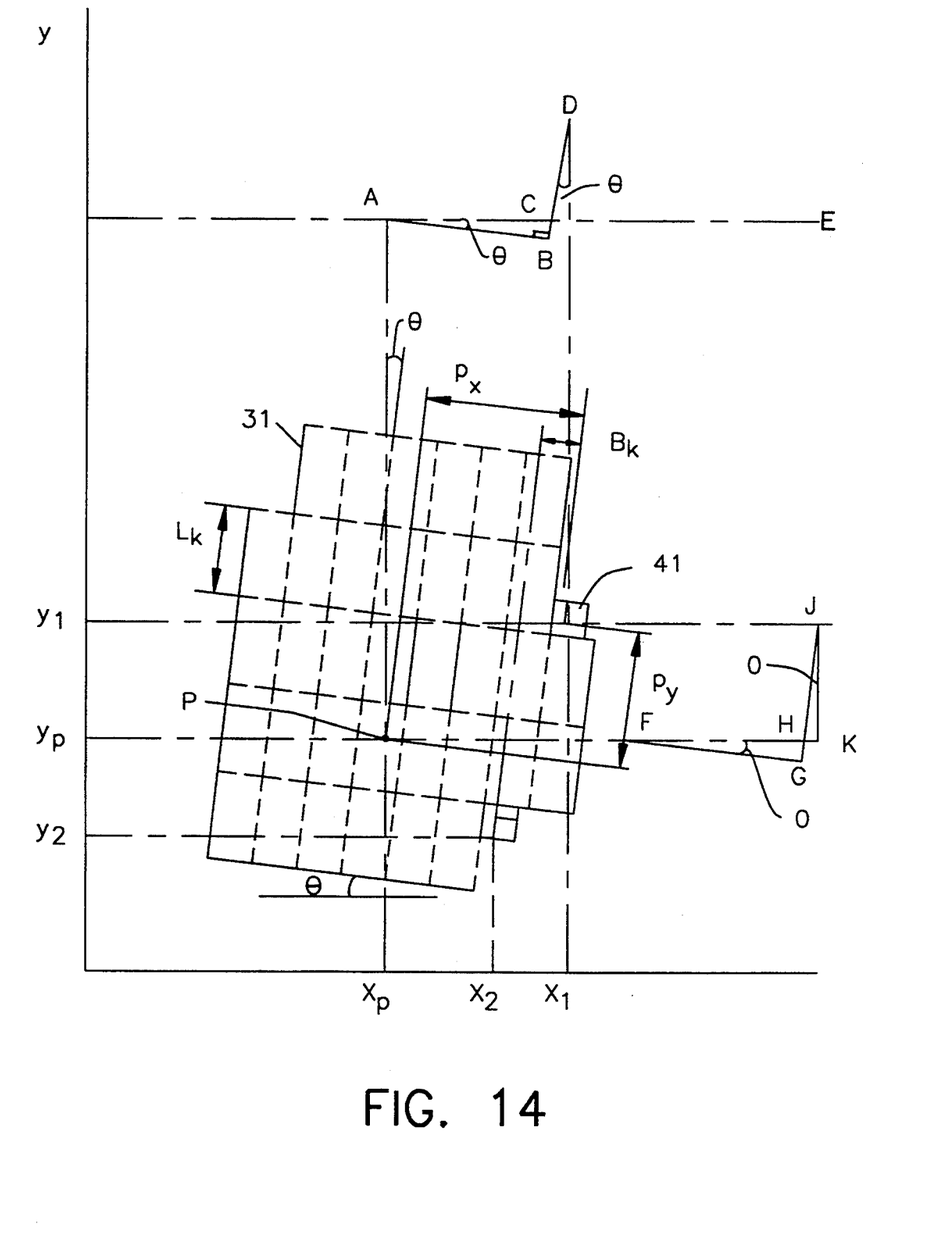
FIG. 14 is a plan view of the carrier plate 31 in a position in which the longitudinal axis of each vessel container is at an angle $\theta$ to the y axis of the coordinate system of the needle-conveying system.

FIG. 14 is a plan view of the carrier plate 31 shown in FIG. 1 in a position in which the longitudinal axis of each vessel container is at an angle $\theta$ to the y axis of the coordinate system of the needle-conveying device. Such a position of the carrier plate 31 may be due e.g. to a somewhat inaccurate arrangement of the carrier plate 31 on the surface 28 of the baseplate 27 in FIG. 1. The carrier plate 31 carries two reference members 41, 42.

In the position of the carrier plate 31 shown in FIG. 14, the coordinates of the reference surfaces of the reference members 41, 42, measured by sensing the reference members 41, 42 with the pipetting needle are:

| Reference member | X coordinate | Y coordinate | Y coordinate |
|---|---|---|---|
| 41 | $x_1$ | $y_1$ | $z_1$ |
| 42 | $x_2$ | $y_2$ | $z_2$ |

As basis for subsequent calculations, the coordinates of the reference members 41, 42 with the pipetting needle for a position of the carrier plate in which the angle $\theta$ is equal to zero, are also measured and stored. These coordinates are as follows:

| Reference member | X coordinate | Y coordinate | Y coordinate |
|---|---|---|---|
| 41 | $\alpha_1$ | $\beta_1$ | $\gamma_1$ |
| 42 | $\alpha_2$ | $\beta_2$ | $\gamma_2$ |

The position of the pipetting needle 11, before being inserted into a primary vessel in order to pipette a volume therefrom, is marked P in FIG. 11. The coordinates of this point are $x_p$, $y_p$ and $z_p$.

To simplify the reasoning, it will first be assumed that the carrier plate 31 is horizontal, i.e. $z_1 = z_2$. In this case $z_p = z_1 - K_z$ where $K_z$ is a constant of the system which defines a suitable positioning of the pipetting needle in the Z direction before the needle has been inserted into the vessel for pipetting.

The coordinates $x_p$ and $z_p$ can be calculated by the following equations:

$$x_p = x_1 - (P_x / \cos \theta) - (P_y - P_x \tan \theta) \sin \theta$$

$$y_p = y_1 - (P_y - P_x \tan \theta) \cos \theta$$

where
$\theta = \text{arc tan } U/V$
where $U = (x_1 - x_2)(\beta_1 - \beta_2) - (Y_1 - Y_2)(\alpha_1 - \alpha_2)$
and $V = (x_1 - x_2)(\alpha_1 \alpha_2) + (y_1 - y_2)(\beta_1 \beta_2)$
$P_x$ and $p_y$ are the distances of point P from the edges of the reference member 41 shown in FIG. 12 in a rectangular system of coordinates, the alignment of which is determined by the grid for receiving the vessel containers 16 on the carrier plate 31. The grid is indicated by broken lines in FIG. 12.

When calculating $x_p$ and $y_p$, the diameter of the needle is neglected, since it is much smaller than $x_p$ or $y_p$.

If the condition $z_1 = z_2$ is not fulfilled, the value $z_p = z_1 - K_z$ can be corrected by allowing for the measured values of $z_1$ and $z_2$.

In FIG. 14, $L_k$ denotes the length and $B_k$ the width of one of the glass containers 16 in FIG. 2.

As the preceding shows, the adjustment of the needle-conveying device according to the invention enables the coordinates of the pipetting position of the needle to be exactly calculated even when the carrier plate 31 has been disposed somewhat inaccurately on the baseplate 27. The calculated coordinates enable the conveying device to move the needle to the right position, i.e. exactly above the middle of the cover on the primary vessel 13, 14, 15 from which a given volume of liquid is to be taken.

Figure 15:
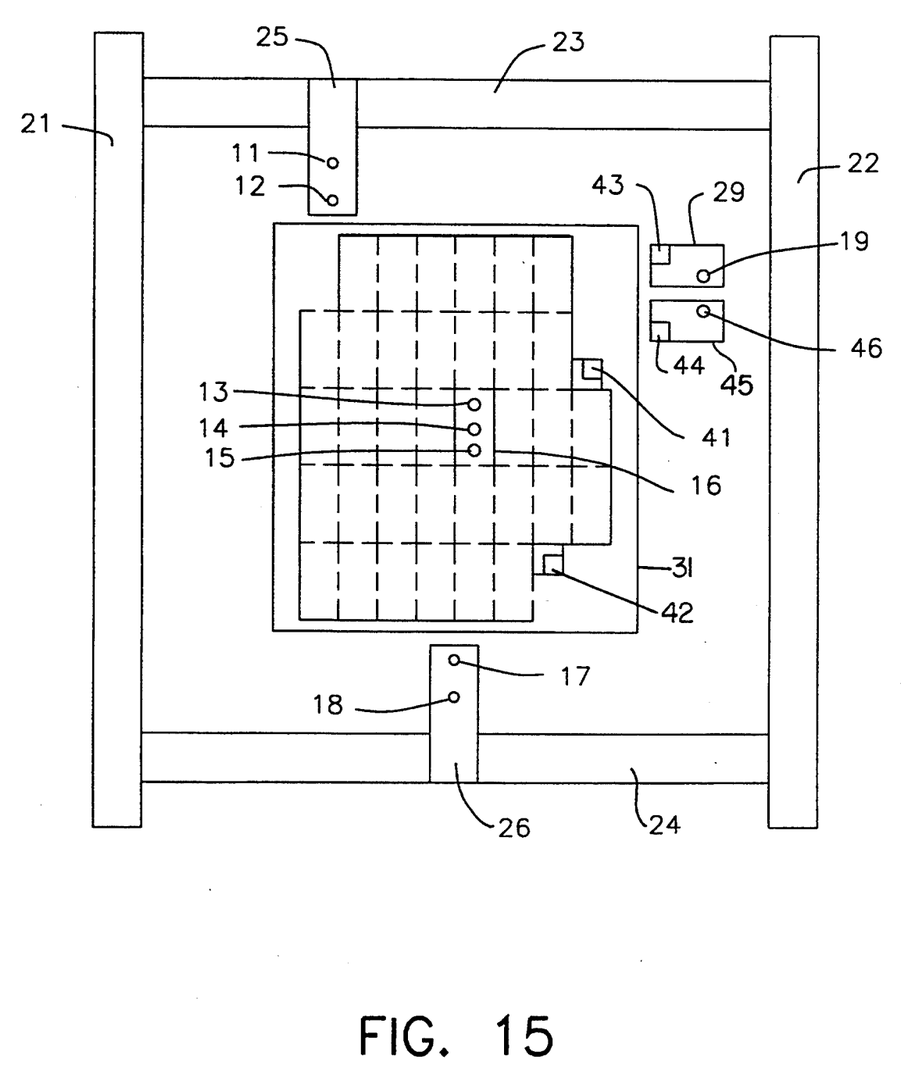
FIG. 15 is a plan view of a variant of the pipetting device in FIG. 1.

FIG. 15 is a plan view of a variant of the pipetting device shown in FIG. 1. In this variant, two identical needle-conveying devices are provided, which basically have the same structure as that shown in FIG. 1 and already described above. In the variant according to FIG. 15, however, each carriage 25, 26 does not carry just one, but two pipetting needles 11, 12, 17, 18. In the variant shown in FIG. 15, an additional processing device 45 is provided to the processing device 29 and reaction vessel 19 shown in FIG. 1, and carries a reaction vessel 46 and a reference member 44. The distance between the pipetting needles guided by a carriage 25, 26 is equal to the distance between the pipetting positions of the processing devices 29 and 45. With this variant, therefore, it is possible to pipette reagents simultaneously to two different reaction vessels using one of the transfer devices.

In the aforementioned pipetting device, a method according to the invention is used for automatically conveying a needle of an automatic pipetting device to a number of pipetting positions, using a conveying device. In the method, each pipetting position corresponds to the position of a given vessel disposed in the pipetting device on a vessel carrier unit, the conveying device being designed to move the needle in three directions X, Y, Z perpendicular to one another, and each direction being parallel to one of the coordinate axes of the conveying device.

In the method according to the invention, at least one reference member is used to determine the coordinates of the pipetting positions for a given position of each vessel carrier unit in the pipetting device, and flat surfaces of the at least one reference member are sensed with the pipetting needle in order to measure coordinates of reference points.

In a preferred embodiment, the method according to the invention comprises the following steps:
a) measuring the coordinates of reference points defined by the positions of the surfaces of the at least one reference member for a given position of the vessel carrier unit in the pipetting device, the measurement being made by causing the conveying device to guide the pipetting needle to each surface of the reference members until it touches this surface, whereupon a signal is generated indicating the contact, and the signal is used to generate and store a coordinate value of the reference point,
b) calculating the coordinates of each pipetting position of the needle in dependence on the measured coordinates of the reference points,
c) storing the calculated coordinates of each pipetting position for the given position of the vessel carrier unit in the pipetting device, and
d) using the stored coordinates of each pipetting position to control the conveying device when the device is used to convey the needle to a given pipetting position.

In another embodiment suitable particularly for pipetting operations in respect of pipetting positions distributed over a certain area, the method according to the invention comprises the following steps:
a) Positioning a removable carrier plate which carries an arrangement of vessels and an arrangement of reference members, in the pipetting device,
b) Measuring coordinates of reference points defined by the positions of the surfaces of at least two reference members for a given position of the carrier plate in the pipetting device, the measurement being made by causing the conveying device to guide the pipetting needle to surfaces of the reference members until it touches said surfaces, whereupon a signal is generated to signal this contact and this signal is used to generate and store a coordinate value of the reference point,
c) calculating the coordinates of each pipetting position of the needle in dependence on the measured coordinates of the reference points,
d) Storing the calculated coordinates of each pipetting position for the given position of the carrier plate,
e) Using the stored coordinates of each pipetting position to control the conveying device when the latter is used to convey the pipetting needle to a given pipetting position Before the above-described method is performed, i.e. before the surfaces of the at least one reference member are sensed with the pipetting needle, rough adjustment of the needle-conveying device and cleaning of the pipetting needle are preferably carried out. This rough adjustment enables the conveying device to perform the sensing of the reference members with the pipetting needle as provided by the invention. Cleaning of the pipetting needle ensures that no impurity (dirt, damp) occurring during operation can affect the reliability of detection of the contacts (contacts between the needle and reference member) and hence the reliability of the adjustment according to the invention.

For the rough adjustment of the conveying device, the pipetting needle is guided into an end position in each of the three directions (Z, X, Y) perpendicular to one another, first in the Z direction and then in the X and Y direction. Each end position is defined by a corresponding stop. The coordinates of each end position are detected and stored. Cleaning of the pipetting needle comprises washing and drying the same.

In performing the sensing of the surfaces of each of the reference members with the pipetting needle in accordance with the invention, preferably a horizontal surface of the reference member is first sensed to determine a reference point in the vertical direction (Z direction). Vertical surfaces of the reference member are then sensed to determine reference points in the other two directions (X and Y direction).

In pipetting devices according to FIG. 15, in which two pipetting needles are guided simultaneously, all the method steps are carried out with the pipetting needle and on the basis of the measured coordinates of the reference points the distance between the pipetting needles and the deviation of this distance from a set value are calculated. Any deviation in excess of a critical value is signalled. Thereby it is indicated that one of the pipetting needles or both of them have a deformation which is too large and therefore unacceptable. Whether a pipetting needle has such a deformation is verified by visual inspection. After replacement of any defective needle the process for adjustment of the needle-conveying system is repeated.

Another variant of the method according to the invention is described hereinafter with reference to FIG. 12. In this variant after measuring the coordinates of reference points, the needle-conveying device is made to guide the pipetting needle 11 through a straight bore 48 in a test member 47, which is connected with a reference member 41 in such a way that the position of the test member and hence the position of the bore is defined by the position of the at least one reference member. Any contact between the pipetting needle and the test member in the introduction of the pipetting needle through the bore is detected and signalled by suitable electrical means 49. If during the guided movement of the pipetting needle through the straight bore in the test member no contact between the needle and the test member is signalled, this fact confirms that the pipetting needle has not a deformation which is unacceptably large, that the needle-conveying device is adjusted with sufficient accuracy, and that therefore it can be assumed that the immediately preceding steps of the process for adjusting the needle-conveying device were carried out properly. If during the guided movement of the pipetting needle through the straight bore in the test member a contact between the needle and the test member is signalled, this fact indicates that the pipetting needle has a deformation which is unacceptably large and/or that the needle-conveying device is not adjusted with sufficient accuracy, and that therefore it can be assumed that the immediately preceding steps of the process for adjusting the needle-conveying device were not carried out properly. Whether a pipetting needle has an unacceptably large deformation is verified by visual inspection. After replacement of any defective needle the process for adjustment of the needle-conveying system is repeated; If after this repetition contact of the needle with the test member is signalled during the guided movement of the needle through the bore, this fact indicates that the immediately preceding steps of the process for adjusting the needle-conveying device were not carried out properly. In this case a more detailed search for the cause of erroneous operation during the process is necessary.

What is claimed is:

1. A pipetting device for pipetting fluid between a primary vessel and a secondary vessel contained in one or more vessel containers, the device comprising:
    (a) at least one removable vessel carrier unit configured and dimensioned to carry one or more vessel containers each having a defined position relative to its vessel carrier unit;
    (b) a baseplate having a surface on which the at least one removable vessel carrier unit can be placed;
    (c) an electrically conductive pipetting needle constructed and positioned for transferring a volume of liquid from one primary vessel to one secondary vessel when the primary vessel and the secondary vessel are contained in one or more of the at least one vessel container placed on the surface of the at least one carrier unit and the at least one carrier unit is placed on the surface of the baseplate;
    (d) means for controllably moving the pipetting needle in three dimensions, thereby bringing the pipetting needle to a predetermined pipetting position;
    (e) at least two electrically conductive reference members secured to each vessel carrier unit, each reference member having a plurality of flat surfaces;
    (f) control means for causing the pipetting needle to be conveyed to the plurality of flat surfaces of the at least two reference members; and
    (g) means for electrically detecting contact between the pipetting needle and each of the plurality of flat surfaces of the at least two reference members.

2. The pipetting device according to claim 1, wherein the means for electrically detecting contact between the pipetting needle and each said surface of the at least two electrically conductive reference members comprise a level sensor.

3. The pipetting device according to claim 1, wherein the at least two electrically conductive reference members each have three surfaces perpendicular to one another, the position of each surface defining the coordinate of a reference point in one of the three dimensions.

4. The pipetting device according to claim 3, wherein each of the three surfaces is flat.

5. A pipetting device comprising:
    (a) at least one removable vessel carrier unit configured and dimensioned to carry a plurality of vessels, with each vessel having a defined position relative to the vessel carrier unit carrying it;
    (b) a pipetting needle connected to a metering device, the pipetting needle being constructed and dimensioned for transferring a volume of liquid from a primary vessel to a secondary vessel when the primary vessel and the secondary vessel are disposed on one or more of the at least one vessel carrier unit;
    (c) a conveyance control device coupled to the pipetting needle for controllably moving the pipetting needle in three dimensions, thereby bringing the pipetting needle to predetermined pipetting positions;
    (d) means for controlling the operation of the metering device and the conveyance control device;
    (e) at least one reference member which is either part of each of the at least one vessel carrier unit or is directly and permanently connected thereto, the at least one reference member having flat surfaces which are capable of being sensed with the pipetting needle;
    (f) control means contained within the conveyance control device for causing the pipetting needle to be conveyed to a plurality of the flat surfaces of the at least one reference member;
    (g) means for detecting contact between the pipetting needle and each of the plurality of flat surfaces of the at least one reference member, the surfaces each defining a reference point;
    (h) a test member connected to one of the at least one reference member, the test member having a straight bore of a diameter larger than the diameter of the pipetting needle;
    (i) means for causing the pipetting needle to be introduced through the bore; and
    (j) means including an electric circuit, for providing a signal if the pipetting needle contacts the test member.

6. The pipetting device according to claim 5, wherein the means for providing a signal if the pipetting needle contacts the test member comprise a level sensor.

7. A pipetting device comprising:
    (a) at least one removable vessel carrier unit configured and dimensioned to carry a plurality of vessels, with each vessel having a defined position relative to the vessel carrier unit carrying it;
    (b) a pipetting needle connected to a metering device, the pipetting needle being constructed and positioned for transferring a volume of liquid from a primary vessel to a secondary vessel when the primary vessel and the secondary vessel are disposed on one or more of the at least one vessel carrier unit;
    (c) a conveyance control device coupled to the pipetting needle for controllably moving the pipetting needle in three dimensions, thereby bringing the pipetting needle to predetermined pipetting positions;
    (d) means for controlling the operation of the metering device and the conveyance control device;
    (e) at least one reference member positioned on the at least one vessel carrier unit, the at least one reference member having flat surfaces which are capable of being sensed with the pipetting needle;
    (f) control means contained within the conveyance control device for causing the pipetting needle to be conveyed to a plurality of the flat surfaces of the at least one reference member;
    (g) means for detecting contact between the pipetting needle and each of the plurality of flat surfaces of the at least one reference member, the surfaces each defining a reference point;

(h) a test member connected to one of the at least one reference member, the test member having a straight bore of a diameter larger than the diameter of the pipetting needle;

(i) means for causing the pipetting needle to be introduced through the bore; and (j) means including an electric circuit, for providing a signal if the pipetting needle contacts the test member.

8. The pipetting device according to claim 7, wherein the means for providing a signal if the pipetting needle contacts the test member comprise a level sensor.

9. A pipetting device comprising:

(a) at least one removable vessel carrier unit configured and dimensioned to carry a plurality of vessels, with each vessel having a defined position relative to the vessel carrier unit carrying it;

(b) a pipetting needle connected to a metering device, the pipetting needle being constructed and dimensioned for transferring a volume of liquid from a primary vessel to a secondary vessel when the primary vessel and the secondary vessel are disposed on one or more of the at least one carrier unit;

(c) a conveyance control device coupled to the pipetting needle for controllably moving the pipetting needle in three dimensions, thereby bringing the pipetting needle to predetermined pipetting positions;

(d) means for controlling the operation of the metering device and the conveyance control device;

(e) at least one reference member positioned on the at least one vessel carrier unit, the reference member having flat surfaces which are capable of being sensed with the pipetting needle;

(f) a test member connected to one of the at least one reference member, the test member having a straight bore of a diameter larger than the diameter of the pipetting needle;

(g) means for causing the pipetting needle to be introduced through the bore; and (h) means including an electric circuit, for providing a signal if the pipetting needle contacts the test member.

10. The pipetting device according to claim 9, wherein the means for providing a signal if the pipetting needle contacts the test member comprise a level sensor.

* * * * *